United States Patent [19]

Simon et al.

[11] Patent Number: 4,464,235

[45] Date of Patent: Aug. 7, 1984

[54] CARRYING OUT ELECTROMICROBIAL REDUCTIONS

[75] Inventors: Helmut Simon, Freising; Johann Bader, Neufahrn; Helmut Güenther, Haag, all of Fed. Rep. of Germany

[73] Assignee: BASF Aktiengesellschaft, Fed. Rep. of Germany

[21] Appl. No.: 513,838

[22] Filed: Jul. 14, 1983

[30] Foreign Application Priority Data

Jul. 17, 1982 [DE] Fed. Rep. of Germany ....... 3226888

[51] Int. Cl.$^3$ .............................................. C25B 3/00
[52] U.S. Cl. .................................... 204/73 R; 435/173
[58] Field of Search .............. 435/173; 204/72, 73 R, 204/75, 76, 77

[56] References Cited

U.S. PATENT DOCUMENTS 4,318,784 3/1982 Higgins ................................ 204/72

OTHER PUBLICATIONS

Weibel et al., Archives of Biochemistry and Biophysics, 169, 146-151, (1975).

Chem. Abstracts, vol. 88, (1978), Nos. 101405h, 101406j, 101407k.

Helmut Simon et al., "Elektro-enzymatische and elektro-mikrobielle stereospezifische Reduktionen", *Angew. Chem.,* vol. 93, No. 10, (1981), pp. 897-898.

Robert DiCosimo et al., "Enzyme-Catalyzed Organic Synthesis: Electro-chemical Regeneration of NAD(P)H from NAD(P) Using Methyl Viologen and Flavoenzymes", *J. Org. Chem.,* 1981, vol. 46, 4622-4623.

Masahide Ito et al., "Spectroelectrochemical Study of Indirect Reduction of Triphophopyridine Nucleotide", *J. Electroanal. Chem.,* vol. 32, 1971, pp. 415-425.

*Primary Examiner*—John F. Niebling
*Attorney, Agent, or Firm*—Keil & Weinkauf

[57] ABSTRACT

An electromicrobial reduction with the aid of aerobic microorganisms in the absence of oxygen is described.

1 Claim, No Drawings

CARRYING OUT ELECTROMICROBIAL REDUCTIONS

The present invention relates to a method of carrying out electromicrobial reductions with the aid of microorganisms which receive the reduction equivalents via an electron carrier which is regenerated electrochemically.

It is known that chemical substances can be reduced electromicrobially, in accordance with the following equation:

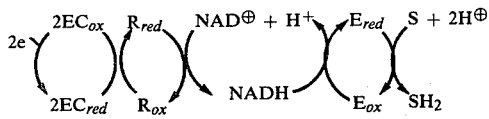

Electrons e are transferred to an electron carrier $EC_{ox}$ which passes them on to a reductase R which reduces, for example, oxidized nicotinamide adenine dinucleotide (NAD$^\oplus$→NADH); cf. J. Elektroanal. Chem. 32 (1971), 415 and J. Org. Chem. 46 (1981), 4623). This NADH can serve as a reducing agent, together with a second enzyme E, which reduces the desired substrate S. However, the costs of enzyme concentration and the instability of pure enzymes prevent the use of these methods for preparative purposes. Attempts have therefore been made to carry out the reduction using whole anaerobic cells which contain reductase (Angew. Chem. 93 (1981), 897). This process, too, is scarcely more suitable for large-scale syntheses, because anaerobic microorganisms are sensitive to oxygen, and their growth and use therefore entail particularly expensive procedures.

The present invention relates to a method of carrying out electromicrobial reductions with the aid of microorganisms which receive the reduction equivalents via an electron carrier which is regenerated electrochemically, wherein the microorganisms employed are aerobic or microaerophilic ones, and the reduction is carried out in the absence of oxygen.

The novel electromicrobial reduction takes place in accordance with the following equation:

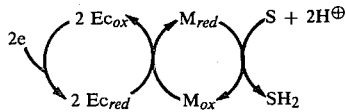

The electrons e originate from a current source and are transferred to an electron carrier $EC_{ox}$, which passes them on to the aerobic microorganism $M_{ox}$. This microorganism transfers the electrons together with two protons to the substrate S, which is reduced to $SH_2$.

Where the cells of the aerobic microorganism contain a reductase which can be reduced by the electrochemically regenerated electron carrier EC, the reduction proceeds very smoothly. However, there are also microorganisms which contain NADH-dependent or NADPH-dependent reductases, including microorganisms which become permeable to NADH or NADPH under the reaction conditions and slowly lose these compounds. Microorganisms which contain enzymes which slowly decompose these pyridine nucleotides also exist. In the last two cases, it is advisable to accelerate the reaction by adding a small amount of a pyridine nucleotide to the reaction mixture.

The reduction is preferably carried out in a compartmented cell at from 5° to 90° C., advantageously from 10° to 50° C., preferably from 20° to 40° C., and at a pH of from 3 to 10, preferably from 5 to 8. The electrodes are produced from electrode material conventionally used in electrosynthesis. For example, cathodes consisting of a metal, eg. lead, copper, iron, nickel, mercury or a steel or graphite semiconductor, or of Nafion doped with a viologen dye, and anodes consisting of platinum or graphite or dimensionally stable anodes of doped or coated titanium, as used for the production of oxygen or chlorine, are suitable. The partition between the anolyte and the catholyte is a commercial diaphragm or membrane, preferably an ion-exchange membrane, as used, for example, for chlor-alkali electrolysis or for electrodialysis. The current density is from 1 to 200, preferably from 1 to 100, mA/cm$^2$, the cathode potential is from $-0.1$ to $-1.5$ V, preferably from $-0.5$ to $-0.9$ V, with reference to standard calomel electrodes, and the terminal voltage of the cell is from 2 to 90 V, preferably from 4 to 20 V.

The electrolysis is carried out as a rule in an aqueous mixture which, in addition to the microbial system and the substrate, can also contain conductive salts, buffers and organic solvents or solubilizers, for example alcohols, such as methanol or ethanol, ethers, such as dioxane, dimethoxyethane or methyl tert.-butyl ether, emulsifiers, such as polyoxyethylene sorbitan monooleate, esters, such as ethyl acetate, alkanes, such as hexane or petroleum ether, chlorohydrocarbons, such as methylene chloride, carbon tetrachloride or chloroform, or dimethylformamide. Organic solvents may be used, particularly in combination with immobilized cells. Examples of such solvents are saturated alcohols, dioxane, furan, dimethylsulfoxide, etc. Furthermore, the procedure may be carried out in a multi-phase system, one phase comprising a hydrocarbon, ether or higher alcohol.

The use of an organic solvent can be advantageous if this allows a heterogeneous reaction procedure (eg. solid/liquid) to be avoided. Where the reaction results in a product which is soluble in organic solvents and which attacks by the microorganism or the enzyme present in this, it may be appropriate to carry out the procedure using a 2-phase system.

Usually, the anolyte consists of an aqueous salt solution, examples of suitable salts for this solution being NaCl, Na$_2$SO$_4$ and NaO—CO—CH$_3$. Instead of the salt solution, it is also possible to use a dilute aqueous mineral acid. As a rule, the catholyte also consists of a salt solution, which additionally contains the substrate and the microorganism. The use of a buffer, such as a phosphate buffer, is advantageous.

Suitable electron carriers are:
1. Viologen dyes, eg. methyl viologen, benzyl viologen and diquat,
2. anthraquinone and other quinone dyes, eg. phenosafranine, methylene blue and 2-anthraquinonesulfonic acid,
3. triphenylmethane dyes, eg. methyl violet and crystal violet,
4. phthalocyanines, eg. Fe phthalocyanine, Cu phthalocyanine and Co phthalocyanine,
5. methine dyes, eg. astraphloxin,
6. pyrrole dyes or porphyrin derivatives, eg. metal chelates of these compounds, 7. pteridines and pteridones,
8. flavins, eg. acriflavin and lumiflavin,
9. imidazole derivatives, eg. metronidazole,
10. complexes of metals of sub-groups 6, 7 and 8, eg. $Ru(L_2L'_2)^{++}$ [L = 1,10-phenanthroline, 2,2-bipyridyl or 5-nitro-1,10-phenanthroline, and L' = pyridine or 4-methylpyridine], 1,1'-bis-(hydroxymethyl)-ferrocene or ferrocenemonocarboxylic acids,
11. thiolates of metals of sub-groups 6, 7 and 8,
12. thiols, eg. dihydroliponic acid, dithiothreitol, 2-mercaptoethanol, glutathione, thiophenol and butane-1,4-dithiol, and
13. $NAD^+$ or $NADP^+$ or their derivatives.

Among these, the 1st group is preferred, and methyl viologen and benzyl viologen are particularly preferred.

Suitable microorganisms for the reduction reaction are all aerobic microorganisms which contain the enzymes required for the desired reaction. Important examples of microorganisms are:

(A) Procaryotes:

Gram-negative aerobic bacteria, eg. *Acetobacter ascendens, Acetobacter pasteurianus, Alcaligenes eutrophus, Pseudomonas aeruginosa, Pseudomonas fluorescens* and *Pseudomonas testosteroni*, Gram-negative facultatively anaerobic bacteria, eg. *Enterobacter aerogenes, Enterobacter agglomerans, Escherichia coli*, Flavobacterium spec., *Proteus mirabilis, Proteus vulgaris, Proteus mitajiri* and *Zymomonas mobilis*, Gram-positive cocci, eg. *Leuconostoc mesenteroides, Peptococcus aerogenes, Sarcina lutea* and *Streptococcus faecalis*, endospore-forming bacteria, eg. *Bacillus subtilis, Bacillus cereus* and *Bacillus polymyxa*, Gram-positive asporogenic bacteria, eg. *Lactobacillus buchneri*, coryneform bacteria, eg. Arthrobacter spec. and *Corynebacterium simplex*, and actinomycetes, eg. *Actinomyces globosus*, Mycobacterium spec., *Nocardia corallina, Streptomyces platensis* and *Streptomyces lavendulae*;

(B) Eucaryotes:

Phycomycetes, eg. *Absidia orchidis, Rhizopus arrhizus, Rhizopus nigricans* and *Rhizopus reflexus*, protoascomycetes (yeasts), eg. *Candida pseudotropicalis, Geotrichum candidum, Hansenula capsulata, Kloeckera magna, Kluyveromyces fragilis, Rhodotorula mucilaginosa, Rhodotorula glutinis, Saccharomyces cerevisiae, Saccharomyces sake, Saccharomyces fragilis, Saccharomyces uvarum, Schizosaccharomyces pombe, Candida utilis* and *Candida boidenii*, ascomycetes, eg. *Aspergillus niger, Aspergillus nidulans, Cladosporium butyri*, Claviceps spec., *Dipodascus albidus*, Eremothecium spec. and *Penicillium chrysogenum*, and Fungi imperfecti, eg. *Curvularia falcata, Epicoccum oryzae, Fusarium lateritium, Fusarium solani* and Phialophora spec.

For the purposes of the present invention, microorganisms are also aerobic protozoa and aerobic cells of higher plants and animals, provided that these can be grown like microorganisms. Such microorganisms can, for example, be obtained from depositories or be self-grown.

Among the stated microorganisms, *Proteus mirabilis, Proteus vulgaris, Alcaligenes eutrophus, Bacillus cereus, Geotrichum candidum, Kloeckera magna, Saccharomyces cerevisiae* and *Candida utilis* are particularly preferred.

In some cases, one microorganism is particularly effective in producing NADH or NADPH, while the reductase has a high activity with respect to the conversion of the substrate S in another microorganism, but the latter microorganism has only a low activity with regard to the formation of NADH or NADPH. In these cases, it is advisable to use a mixture of the two microorganisms.

The microorganisms or cells can also be used in immobilized form for the conversions. Furthermore, the permeability of the microorganisms to cosubstrates, substrates and products can be increased in a number of cases, for example by freezing and thawing out the cells.

Although the reduction is carried out using aerobic cells, virtually no oxygen should be present during the reaction. The oxygen content must be sufficiently low that any reaction between the oxygen and the electron carrier which may take place is unimportant, and that the oxygen or an oxidation product formed as a result of the presence of oxygen has no inhibitory effect on the enzymes and cosubstrates present during the reaction. If the oxygen content of the catholyte increases, for example, where methyl viologen is used, to above $5.10^{-7}M$, the current efficiency and the stability of the biocatalysts decrease with increasing oxygen content.

Other examples of electromicrobial reductions according to the invention are:

I. Reductions of carbonyl groups

1. Selective reduction of aldehyde groups in the presence of other reducible functions

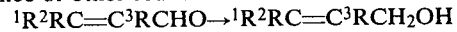

for example, preparation of 2-substituted cinnamic alcohols from the corresponding cinnamaldehydes, hydroxyacetophenone from phenylglyoxal, and other hydroxyketones from diketones.

2. Preparation of primary alcohols which are chiral as a result of the stereospecific substitution of a hydrogen atom by a deuterium or tritium atom; these alcohols are prepared by reduction in deuterium oxide or in tritium-labeled water.

3. Selective reductions of keto groups in the presence of other reducible functions. Examples:

$$C_6H_5CH=CRCOCH_3 \rightarrow C_6H_5CH=CRCHOHCH_3$$

or

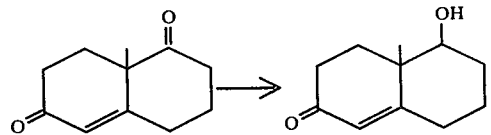

or $\Delta^4$-androstene-3,17-dione to testosterone.

4. Preparation of chiral cyclic and non-cyclic alcohols, hydroxyacids and the like:

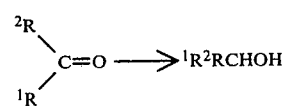

for example, (R)-mandelic acid from phenylglyoxylic acid, or (R)-phenyllactate from phenylpyruvate. Where appropriately substituted ketones or cycloketones are reduced using substrate-specific and product-specific enzyme systems, resolution of the racemate may take place at the same time.

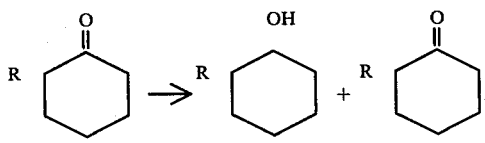

Depending on the specificity of the enzyme system, one of three further pairs can be obtained.

II. Selective reduction of unsaturated groups in prochiral or achiral molecules 1. Selective reductions in the presence of other reducible groups, for example reductions of sorbic acid to $\Delta^4$-pentenecarboxylic acid, or of $\alpha,\beta$-unsaturated aldehydes to saturated aldehydes.

2. Reductions of $\alpha,\beta$-unsaturated carbonyl and carboxyl compounds, in particular those which are appropriately substituted and hence lead to chiral products
$$R^1R^2C=CXY \rightarrow R^1R^2CHCHXY$$

In the formulae, Y is COO—, CHO or COR, X is H, alkyl, alkoxy, alkylthio, halogen, dialkylamino or arylamino, and $R^1$ and $R^2$ are each H, alkyl, alkoxy, aryl, alkoxycarbonyl or alkenyl.

Particular examples of such hydrogenation products are chiral halocarboxylic acids, eg. 3-(p-chlorophenyl)-2-chloropropionic acid, chiral $\alpha$- and $\beta$-alkyl-branched carboxylic acids, eg. (R)- and (S)-2-methyl-3-phenylpropionic acid and 2-amino-3-methyl-3-phenylpropionic acid, and $\Delta^3$-2- and/or 4-substituted carboxylic acids obtained from the corresponding allenecarboxylic acids. A racemate (molecular asymmetry) can be converted to chiral E/Z isomers, which can be readily separated.

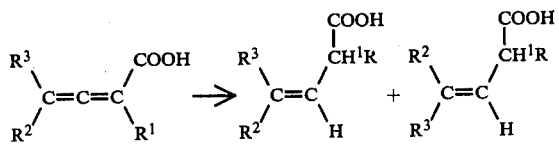

Examples of the reduction of aldehydes to chiral products include the preparation of (R)- or (S)-citronellal or citronellol from cis- or trans-citral.

3. Reduction of isolated C=C double bonds, which when appropriately substituted can also lead to chiral compounds.

4. Reductions of C=C double bonds in labeled water, in order to obtain compounds which become chiral when H in a methylene or methyl group is stereospecifically replaced by $^2H$ or $^3H$, eg. [2,3-$^2H$]-dideuterobutyrate or [2,3-$^2H$]-dideuterophenylpropionate. A chiral methyl group can be obtained by reducing (E)- or (Z)-CH3H=CHCOOH in $^2H_2O$.

III. Reductive amination of carbonyl compounds, in particular of ketoacids to amino acids, eg. the conversion of 2-oxo-5-methylpentanecarboxylic acid to (S)-leucine.

The end product is isolated from the reaction solution in a conventional manner, for example by distillation, extraction, crystallization or chromatography.

Compared with methods carried out using anaerobic microorganisms, the novel method has the following advantages:

Aerobic microorganisms are insensitive to oxygen and hence much easier to use.

Aerobic microorganisms are simpler to produce than anaerobic ones. Moreover, they give substantially higher cell densities, so that less expense is entailed with regard to the apparatus required to produce them.

Furthermore, it could not be foreseen that it would be possible to carry out reactions using aerobic microorganisms without passing oxygen into the reaction medium, since as a rule reactions involving such microorganisms take place only when vigorous aeration is carried out.

It is not necessary to add any carbohydrates to the reaction medium. By-products, which have to be separated off, are therefore not formed.

The Examples which follow illustrate the invention. In every Example, the electromicrobial reduction was carried out in the absence of atmospheric oxygen. The electrolysis cell used is described in Angew. Chem. 93 (1981), 897.

EXAMPLE 1

Preparation of (2R)-propanediol

50 $\mu$mole of methyl viologen, 2.5 millimoles of potassium phosphate and 400 mg of *Candida utilis* (eg. DSM 70,167) were dissolved or suspended in 25 ml of water, and the pH was brought to 7.0. The resulting mixture was introduced into an electrochemical cell, and the methyl viologen was reduced at a constant cathode potential of $-790$ mV with reference to a standard calomel electrode (SCE). The zero current was about 0.25 mA. Thereafter, 1 millimole of acetol was added, and the potential was maintained at $-790$ mV. After 50 hours, the acetol had been quantitatively converted to (2R)-propanediol, which was separated off by distillation after the mixture had been centrifuged. The (2R)-propanediol had an optical rotation $[\alpha]_D^{20}$ of $-20.7°$.

EXAMPLE 2

Preparation of (2R)-propanediol

In this Example, the starting mixture used in Example 1 was employed, except that 19 $\mu$moles of NAD$^\oplus$ were added. 4 millimoles of acetol were added to the solution containing the reduced methyl viologen, and the voltage was maintained at $-790$ mV. After 22 hours, a further 19 $\mu$moles of NAD$^\oplus$ were added in order to increase the current, which in the meantime had fallen to about 2.5 mA. After 45 hours, the acetol had been completely converted to (2R)-propanediol, which was isolated and characterized as described in Example 1. $[\alpha]_D^{20} = -20.5$.

EXAMPLE 3

Preparation of (R)-pantolactone

250 $\mu$moles of sodium 2-ketopantoate were reduced by a procedure similar to that described in Example 2, except that 6.4 $\mu$moles of NAD$^\oplus$ were added, and this addition was repeated after 30 hours and 50 hours. After 70 hours, quantitative conversion had taken place. The (R)-pantolactone formed on acidification was extracted with ether and sublimed. In the presence of a chiral shift reagent, it was more than 99.5% optically pure, measured by NMR spectroscopy.

The same reaction could also be carried out using benzyl viologen at a cathode potential of $-620$ mV with reference to the SCE.

The reduction could also be carried out using *Proteus mirabilis* (DSM 30,115) and *Proteus vulgaris* (DSM 30,118). In these cases, a current of 15 mA per 20 mg of cell material was obtained.

EXAMPLE 4

Preparation of (R)-methylsuccinic acid

180 μmoles of methyl viologen, 9 millimoles of potassium phosphate, 9 μmoles of EDTA and 1.11 g of E.coli (K 12, obtainable from the Deutsche Sammlung von Mikroorganismen, Göttingen) were dissolved or suspended in a little water, and the pH was brought to 7.0. Thereafter, the mixture was made up to 90 ml with water, and 1.6 millimoles of a mesaconate were added. The resulting mixture was reduced at −790 mV, by a procedure similar to that described in Example 1. After 42.5 hours, 98.5% conversion to (R)-methylsuccinic acid had taken place, and this product was isolated by extracting the acidified solution with ether. The product had an optical rotation $[\alpha]_D^{20}$ of +9.2°.

EXAMPLE 5

Preparation of propanediol

160 μmoles of methyl viologen and 4 millimoles of a tris-(hydroxymethyl)-aminomethaneacetate were dissolved in 40 ml of water, and the pH was brought to 7.0. This solution was reduced in an electrochemical cell at a constant cathode potential of −700 mV. Thereafter, 0.5 ml of a suspension of *Bacillus cereus* (DSM 31), corresponding to a dry weight of 10 mg, 32 μmoles of NAD, 1,200 μmoles of acetol and 0.3 ml of a suspension of *Alcaligenes eutrophus* H 16 (DSM 428), corresponding to a dry weight of 2.0 mg, were added. In the complete system, the current flow was 4.5 mA. More than 90% of the acetol employed was reduced in the course of 18 hours.

The same conversion could be achieved using *Candida utilis* and *Alcaligenes eutrophus* in combination. In this reaction, the reduction rate achieved per unit weight of biocatalyst (sum of the two organisms) is about 10 times higher than in Example 1.

EXAMPLE 6

Reduction of phenylpyruvate or 2-oxo-4-methylpentanate to the corresponding 2-hydroxyacids The crude lysates of the two microorganisms mentioned in Example 5 and the other components, as well as the phenylpyruvate or 2-oxo-4-methylpentanate, were converted in an electrochemical cell by a procedure similar to that described in Example 5. During the reduction, the current was about 0.5 mA.

We claim:

1. A method of carrying out an electromicrobial reduction with the aid of microorganisms which receive the reduction equivalents via an electron carrier which is regenerated electrochemically, wherein the microorganisms employed are aerobic or microaerophilic ones, used either alone or in combination with one another, and the reduction is carried out substantially in the absence of oxygen.

* * * * *